(12) United States Patent
Goodwin et al.

(10) Patent No.: US 6,808,533 B1
(45) Date of Patent: Oct. 26, 2004

(54) COVERED STENT AND METHOD OF COVERING A STENT

(75) Inventors: Jonathan L. Goodwin, Nashua, NH (US); Gary A. Jordan, Litchfield, NH (US); Peter H. Gingras, Windham, NH (US)

(73) Assignee: Atrium Medical Corporation, Hudson, NH (US)

( * ) Notice: Subject to any disclaimer, the term of this patent is extended or adjusted under 35 U.S.C. 154(b) by 0 days.

(21) Appl. No.: 09/627,566

(22) Filed: Jul. 28, 2000

(51) Int. Cl.⁷ ................................................. A61F 2/06
(52) U.S. Cl. ........................................................ 623/1.13
(58) Field of Search .................. 623/1.1–1.2; 606/108, 606/191, 194, 198

(56) References Cited

U.S. PATENT DOCUMENTS

| | | | |
|---|---|---|---|
| 3,868,956 A | 3/1975 | Alfidi et al. ................. | 128/345 |
| 4,560,374 A | 12/1985 | Hammerslag ................ | 604/49 |
| 4,562,596 A | 1/1986 | Kornberg ....................... | 623/1 |
| 4,580,568 A | 4/1986 | Gianturco .................... | 128/345 |
| 4,588,461 A | 5/1986 | Braun ......................... | 156/143 |
| 4,647,416 A | 3/1987 | Seiler et al. ................. | 264/118 |
| 4,655,771 A | 4/1987 | Wallsten ........................ | 623/1 |
| 4,733,665 A | 3/1988 | Palmaz ....................... | 128/343 |
| 4,739,762 A | 4/1988 | Palmaz ....................... | 128/343 |
| 4,740,207 A | 4/1988 | Kreamer ....................... | 623/1 |
| 4,776,337 A | 10/1988 | Palmaz ....................... | 128/343 |
| 4,787,899 A | 11/1988 | Lazarus ......................... | 623/1 |
| 4,820,298 A | 4/1989 | Leveen et al. ................. | 623/1 |
| 4,856,516 A | 8/1989 | Hillstead .................... | 128/343 |
| 4,872,874 A | 10/1989 | Taheri ............................ | 623/1 |
| 4,877,030 A | 10/1989 | Beck et al. .................. | 128/343 |
| 4,886,062 A | 12/1989 | Wiktor ....................... | 128/343 |
| 4,907,336 A | 3/1990 | Gianturco .................... | 29/515 |
| 4,950,227 A | 8/1990 | Savin et al. .................... | 604/8 |
| 5,078,726 A | 1/1992 | Kreamer ...................... | 606/194 |
| 5,078,735 A | 1/1992 | Mobin-Uddin ................ | 623/1 |
| 5,100,429 A | 3/1992 | Sinofsky et al. ............ | 606/195 |
| 5,102,417 A | 4/1992 | Palmaz ....................... | 606/195 |
| 5,104,399 A | 4/1992 | Lazarus ......................... | 623/1 |
| 5,122,154 A | 6/1992 | Rhodes ....................... | 606/198 |
| 5,123,917 A | 6/1992 | Lee ................................ | 623/1 |
| 5,133,732 A | 7/1992 | Wiktor ....................... | 606/195 |
| 5,135,536 A | 8/1992 | Hillstead .................... | 606/195 |

(List continued on next page.)

FOREIGN PATENT DOCUMENTS

| | | |
|---|---|---|
| EP | 335 341 | 3/1989 |
| EP | 364 787 | 9/1989 |
| EP | 540 290 | 10/1992 |

(List continued on next page.)

*Primary Examiner*—Vy Q. Bui
(74) *Attorney, Agent, or Firm*—Lahive & Cockfield, LLP (57) ABSTRACT

A radially deployable covered stent that predictably and dependably expands to an increased diameter state at relatively low deployment pressures while concomitantly minimizing the risk of tearing of the stent covering during expansion. The stent covering includes an inner cover and an outer cover that are bonded together through and around the stent structure to cover the stent. The stent cover is constructed from expanded polytetrafluoroethylene (ePTFE) having a structure of nodes interconnected by fibrils. The stent covering has a radial thickness of at least about 0.008" and an average internodal distance (IND) of at least about 100 microns when the stent is in the reduced diameter, unexpanded state. The covered stent deploys at an average deployment pressure of less than or equal to about 10 atm. A method for covering a stent structure according to the present invention includes placing a compression member in the form of a tubular sleeve over the outer cover and heating the compressed covered stent to bond the inner cover to the outer cover. An adhesive in the form of an aqueous dispersion of PTFE can be applied to either the inner cover or the outer cover to facilitate bonding of the inner cover to the outer cover.

12 Claims, 6 Drawing Sheets

U.S. PATENT DOCUMENTS

| | | | |
|---|---|---|---|
| 5,151,105 A | 9/1992 | Kwan-Gett | 623/1 |
| 5,156,620 A | 10/1992 | Pigott | 623/1 |
| 5,213,561 A | 5/1993 | Weinstein et al. | 600/7 |
| 5,219,355 A | 6/1993 | Parodi et al. | 606/191 |
| 5,256,150 A | 10/1993 | Quiachon et al. | 604/171 |
| 5,288,711 A | 2/1994 | Mitchell et al. | 514/56 |
| 5,290,295 A | 3/1994 | Querals et al. | 606/108 |
| 5,292,331 A | 3/1994 | Boneau | 606/198 |
| 5,304,220 A | 4/1994 | Maginot | 623/1 |
| 5,306,286 A | 4/1994 | Stack et al. | 606/198 |
| 5,306,294 A | 4/1994 | Winston et al. | 623/1 |
| 5,314,444 A | 5/1994 | Gianturco | 606/195 |
| 5,314,472 A | 5/1994 | Fontaine | 623/12 |
| 5,316,023 A | 5/1994 | Palmaz et al. | 128/898 |
| 5,330,500 A | 7/1994 | Song | 606/198 |
| 5,334,201 A | 8/1994 | Cowan | 623/1 |
| 5,342,300 A | 8/1994 | Stefanadis et al. | 604/95 |
| 5,366,473 A | 11/1994 | Winston et al. | 606/198 |
| 5,368,556 A | 11/1994 | Lecuyer | 604/8 |
| 5,370,683 A | 12/1994 | Fontaine | 623/1 |
| 5,370,685 A | 12/1994 | Stevens | 623/2 |
| 5,382,230 A | 1/1995 | Bonn | 604/32 |
| 5,382,261 A | 1/1995 | Palmaz | 606/158 |
| 5,387,235 A | 2/1995 | Chuter | 623/1 |
| 5,389,106 A | 2/1995 | Tower | 606/198 |
| 5,391,172 A | 2/1995 | Williams et al. | 606/108 |
| 5,397,355 A | 3/1995 | Marin et al. | 623/12 |
| 5,403,341 A | 4/1995 | Solar | 606/198 |
| 5,405,377 A | 4/1995 | Cragg | 623/1 |
| 5,411,549 A | 5/1995 | Peters | 623/1 |
| 5,415,664 A | 5/1995 | Pinchuk | 606/108 |
| 5,443,458 A | 8/1995 | Eury | 604/891.1 |
| 5,443,496 A | 8/1995 | Schwartz et al. | 623/1 |
| 5,449,373 A | 9/1995 | Pinchasik et al. | 606/198 |
| 5,453,090 A | 9/1995 | Martinez et al. | 604/53 |
| 5,458,615 A | 10/1995 | Klemm et al. | 606/198 |
| 5,466,509 A * | 11/1995 | Kowligi et al. | 428/141 |
| 5,514,154 A | 5/1996 | Lau et al. | 606/195 |
| 5,522,881 A | 6/1996 | Lentz | 623/1 |
| 5,522,882 A | 6/1996 | Gaterud et al. | 623/1 |
| 5,549,663 A | 8/1996 | Cottone, Jr. | 623/1 |
| 5,574,875 A | 11/1996 | Stansfield et al. | 395/403 |
| 5,591,226 A | 1/1997 | Trerotola et al. | 623/1 |
| 5,639,274 A | 6/1997 | Fischell et al. | 604/96 |
| 5,662,700 A | 9/1997 | Lazarus | 623/1 |
| 5,665,114 A | 9/1997 | Weadock et al. | 623/1 |
| 5,667,523 A | 9/1997 | Bynon et al. | 606/198 |
| 5,697,971 A | 12/1997 | Fischell et al. | 623/1 |
| 5,700,285 A | 12/1997 | Myers et al. | 623/1 |
| 5,702,419 A | 12/1997 | Berry et al. | 606/198 |
| 5,718,973 A | 2/1998 | Lewis et al. | 428/36.5 |
| 5,735,892 A | 4/1998 | Myers et al. | 623/1 |
| 5,735,893 A | 4/1998 | Lau et al. | 623/1 |
| 5,747,128 A | 5/1998 | Campbell et al. | 428/35.7 |
| 5,747,728 A | 5/1998 | Fleurial et al. | 136/203 |
| 5,749,880 A * | 5/1998 | Banas et al. | 606/198 |
| 5,755,775 A | 5/1998 | Trerotola et al. | 623/1 |
| 5,788,626 A | 8/1998 | Thompson | 600/36 |
| 5,800,512 A | 9/1998 | Lentz et al. | 623/12 |
| 5,800,522 A | 9/1998 | Campbell et al. | 623/1 |
| 5,810,870 A | 9/1998 | Myers et al. | 606/198 |
| 5,817,126 A | 10/1998 | Imran | 606/198 |
| 5,827,322 A | 10/1998 | Williams | 606/198 |
| 5,836,316 A | 11/1998 | Plaia et al. | 128/898 |
| 5,843,166 A | 12/1998 | Lentz et al. | 623/1 |
| 5,843,171 A | 12/1998 | Campbell | 623/1 |
| 5,843,173 A | 12/1998 | Shannon et al. | 623/1 |
| 5,851,228 A | 12/1998 | Pinheiro | 623/1 |
| 5,851,232 A | 12/1998 | Lois | 623/1 |
| 5,853,419 A | 12/1998 | Imran | 606/191 |
| 5,868,782 A | 2/1999 | Frantzen | 606/198 |
| 5,891,193 A | 4/1999 | Robinson et al. | 623/1 |
| 5,899,935 A | 5/1999 | Ding | 623/1 |
| 5,916,264 A | 6/1999 | Von Oepen et al. | 623/1 |
| 5,921,995 A | 7/1999 | Kleshinski | 606/153 |
| 5,925,075 A | 7/1999 | Myers et al. | 623/1 |
| 5,928,279 A | 7/1999 | Shannon et al. | 623/1 |
| 5,944,726 A | 8/1999 | Blaeser et al. | 606/108 |
| 5,972,441 A | 10/1999 | Campbell et al. | 428/34.1 |
| 5,976,650 A | 11/1999 | Campbell et al. | 428/35.7 |
| 5,980,565 A | 11/1999 | Jayaraman | 623/1 |
| 5,993,489 A | 11/1999 | Lewis et al. | 628/1 |
| 6,001,123 A | 12/1999 | Lau | 623/1 |
| 6,001,125 A | 12/1999 | Golds et al. | 623/1 |
| 6,004,348 A | 12/1999 | Banas et al. | 623/1 |
| 6,010,529 A | 1/2000 | Herweck et al. | 623/1 |
| 6,010,530 A | 1/2000 | Goicoechea | 623/1 |
| 6,015,430 A | 1/2000 | Wall | 623/1 |
| 6,017,362 A | 1/2000 | Lau | 623/1 |
| 6,025,044 A | 2/2000 | Campbell et al. | 428/36.91 |
| 6,027,811 A | 2/2000 | Campbell et al. | 428/411.1 |
| 6,039,755 A | 3/2000 | Edwin et al. | 623/1 |
| 6,086,610 A | 7/2000 | Duerig et al. | 623/1 |
| 6,087,552 A | 7/2000 | Gregory | 623/11 |
| 6,124,523 A | 9/2000 | Banas et al. | 623/11 |
| 6,296,661 B1 * | 10/2001 | Davila et al. | 623/1.13 |

FOREIGN PATENT DOCUMENTS

| | | |
|---|---|---|
| EP | 807 424 | 10/1992 |
| EP | 821921 | 4/1998 |
| EP | 876 806 | 4/1998 |
| EP | 878 174 | 5/1998 |
| WO | WO 97/25938 | 7/1997 |
| WO | WO 98/28035 | 7/1998 |
| WO | WO 98/37833 | 9/1998 |
| WO | WO 99/15108 | 4/1999 |
| WO | WO 00/18328 | 4/2000 |

* cited by examiner

COVERED STENT AND METHOD OF COVERING A STENT

BACKGROUND OF THE INVENTION

Radially expandable stents are commonly used to restore and maintain the patency of body passages, particularly blood vessels. Such stents are provided in a reduced diameter state suitable for percutaneous insertion into the body passage through a catheter. The stent is typically maintained in the reduced diameter state until delivery into the body passage, whereupon the stent is expanded to an increased diameter state within the body passage to hold open the body passage. A catheter delivered balloon is typically used to expand the stent to the increased diameter state.

A biocompatible cover can be provided on the outer and/or inner surfaces of the stent to reduce tissue reactions associated with the expansion of the stent into contact with the walls of the body vessel. Such covers can adversely effect the expansion characteristics of the stent by increasing the deployment pressure necessary to deploy the covered stent to the expanded state. Such covers can also cause asymmetrical expansion of the stent or incomplete expansion of portions or all of the stent. Additionally, deployment of the stent to the expanded state can cause the stent cover to tear and delaminate.

SUMMARY OF THE INVENTION

The present invention provides a covered stent that predictably and dependably expands to an increased diameter state at relatively low deployment pressures while concomitantly minimizing the risk of tearing of the stent covering during expansion. The stent covering is comprised of an inner cover and an outer cover that are positioned adjacent the inner surface and outer surface, respectively, of the stent structure to cover the stent. The inner cover and the outer cover can be constructed from the same or different biocompatible materials, such as, fluoropolymers like expanded polytetrafluoroethylene, having a structure of nodes interconnected by fibrils.

The inventors have determined that decreasing the radial thickness of the covering and increasing the average internodal distance (IND) of the fluoropolymers material forming the stent covering, reduces the deployment pressure necessary to expand the covered stent. However, they also increase the incidence of tearing of the stent covering.

In accordance with one aspect of the present invention, the stent covering has a radial thickness of at least about 0.008" when the stent is in the reduced diameter, unexpanded state.

In accordance with another aspect of the present invention, the average internodal distance of the fluoropolymer material forming either the inner cover or the outer cover is greater than 100 microns when the stent is in the reduced diameter, unexpanded state. In one preferred embodiment, the average IND of the fluoropolymer material forming either the inner cover or the outer cover can be at least about 110 microns. In the most preferred embodiment, the average IND of the fluoropolymer material forming either the inner cover or the outer cover is at least about 135 microns.

In accordance with a further aspect of the present invention, the stent deploys from a reduced diameter configuration to an increased diameter configuration at an average deployment pressure of less than or equal to about 10 atm. In a preferred embodiment, the average deployment pressure of the stent is between about 4 atm and about 8 atm.

The present invention further provides a method for covering a stent structure. The method includes the step of positioning an inner cover of fluoropolymer material within the stent structure adjacent the inner surface of the stent structure and positioning an outer cover of fluoropolymer material over the outer surface of the stent structure. A compression tube is placed over the outer cover and the covered stent structure is heated to bond the inner cover to the outer cover.

The compression tube is preferably a tubular metal sleeve. In a preferred embodiment, a tube of fluoropolymer material is positioned between the outer cover and the compression tube. The compression tube and the tube of fluoropolymer material are removed after the covered stent structure is heated.

An adhesive can be applied to either the inner cover or the outer cover to facilitate bonding of the inner cover to the outer cover. The adhesive is preferably an aqueous dispersion of fluoropolymer material, such as PTFE. The aqueous dispersion can be heated after application to evaporate the aqueous component of the dispersion.

BRIEF DESCRIPTION OF THE DRAWINGS

These and other features and advantages of the present invention will be more fully understood by reference to the following detailed description in conjunction with the attached drawings in which like reference numerals refer to like elements through the different views. The drawings illustrate principles of the invention and, although not to scale, show relative dimensions.

DETAILED DESCRIPTION OF THE PREFERRED EMBODIMENTS

Figure 1:
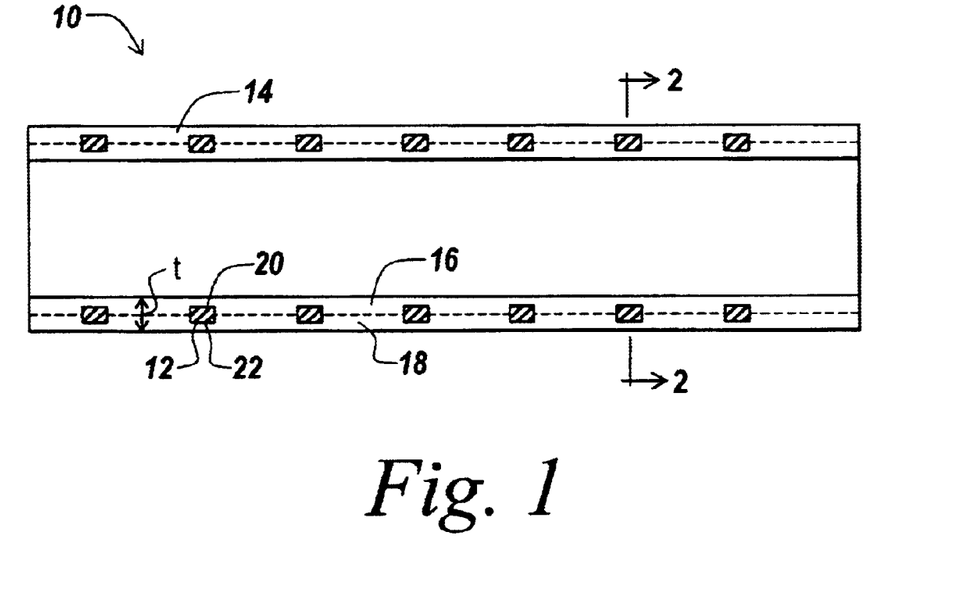
FIG. 1 is a side elevational view in cross-section of a covered stent according to the teachings of the present invention.
Figure 2:
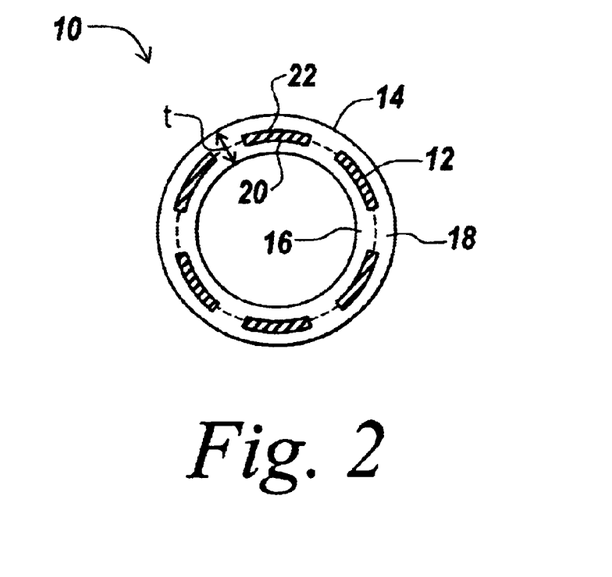
FIG. 2 is a cross-sectional view of the stent of FIG. 1 along the line 2—2.

A radially expandable covered stent 10 in accordance with the teachings of the present invention is illustrated in FIGS. 1 and 2. The covered stent 10 is deployable from a reduced diameter, unexpanded configuration to an increased diameter, expanded configuration. The covered stent 10 is illustrated in FIGS. 1 and 2 in the reduced diameter, unexpanded configuration. The covered stent 10 is comprised of a stent structure 12 and a stent covering 14. The properties of the stent covering 14, described in detail below, as well as the method of covering the stent structure, described in detail below, allow the covered stent 10 to predictably and dependably expand to an increased diameter state at relatively low deployment pressures while concomitantly minimizing the risk of tearing of the stent covering during expansion.

The stent structure 12 can be a balloon expandable slotted stent such as described in U.S. Pat. No. 4,739,762 to Palmaz, incorporated herein by reference, as illustrated in FIGS. 1 and 2. Alternatively, the stents described in commonly-assigned U.S. patent application Ser. No. 09/628,096, filed concurrently herewith, can be employed. Other types of balloon expandable stents that can be used in the present invention include, for example, WITKOR stents described in U.S. Pat. No. 4,969,458, STRECKER stents described in U.S. Pat. No. 5,405,378, or PALMAZ-SCHATZ stents described in U.S. Pat. No. 5,195,984. Alternatively, self-expanding stents, such as, for example, Nitinol stents, stents described in commonly-owned U.S. patent application Ser. No. 09/237,197, filed Jan. 25, 1999, GIANTURCO stents described in U.S. Pat. No. 4,580,568 or WALLSTENTs described in U.S. Pat. No. 4,544,771, can be used in conjunction with the present invention. One skilled in the art will appreciate that the present invention is not limited to any particular stent design, and that any radially expandable stent can be employed in the present invention. All of the above-referenced patents and patent applications are incorporated herein by reference.

The stent covering 14 is comprised of an inner cover 16 and an outer cover 18. The inner cover 16 is positioned within the lumen of the stent structure 12 and contacts the inner surface 20 of the stent structure 12. The outer cover 18 is positioned over the stent structure 12 and contacts the outer surface 22 of the stent structure 12. The inner cover 16 and the outer cover 18 are preferably bonded together in the space between the structural elements forming the stent structure 12. In this manner, the stent cover 14 surrounds and envelops the stent structure 12. It is preferable for the inner cover 16 and the outer cover 18 to extend along the entire length of the stent structure 12, although, in certain applications, it may be desirable to cover only portions or a portion of the length of the stent structure 12.

The inner cover 16 and the outer cover 18 of the stent covering 14 can be constructed from known biologically compatible materials such as, for example, fluoropolymer materials. Various fluoropolymer materials are suitable for use in the present invention. Suitable fluoropolymer materials include, for example, polytetrafluoroethylene (PTFE) or copolymers of tetrafluoroethylene with other monomers. Such monomers include ethylene, chlorotrifluoroethylene, perfluoroalkoxytetrafluoroethylene, or fluorinated propylenes such as hexafluoropropylene. Expanded PTFE (ePTFE) is the preferred material of choice. ePTFE is characterized by a microstructure of nodes interconnected by fibrils and is a hydrophobic, biocompatible, inelastic material having a low coefficient of friction, making ePTFE particularly suited for covering stents.

The inventors have determined that decreasing the radial thickness of the stent covering 14 and increasing the average internodal distance (IND) of the material forming the stent covering 14, reduces the deployment pressure necessary to expand the covered stent 10. However, this also increases the incidence of tearing of the stent covering 14 from expansion. It is desirable for the covered stent 10 to deploy from the unexpanded to the expanded configuration at deployment pressures of less than or equal about 10 atms. The covering applied to conventional stents can increase the deployment pressure necessary to deploy the stent. Conventional covered stents typically deploy at higher deployment pressures. Such higher deployment pressures may not be suitable for all treatment applications, particular the treatment of smaller sized body vessels.

In one preferred embodiment of the covered stent 10 of the present invention, the thickness of stent covering 14, including both the inner and the outer covers 16, 18, is at least about 0.008" when the stent is in the unexpanded configuration. The thickness of the covering 14 is measured between the structural elements of the stent structure 12, as illustrated by arrow t in FIGS. 1 and 2. In addition, the average internodal distance (IND) of the material forming either the inner cover 16 or the outer cover 18 of the stent covering 14 is preferably greater than 100 microns. The average IND of either the inner cover 16 or the outer cover 18 of the stent covering 14 can be at least about 110 microns, and in one preferred embodiment the average IND of either the inner cover 16 or the outer cover 18 is greater than or equal to about 135 microns.

Figure 3:
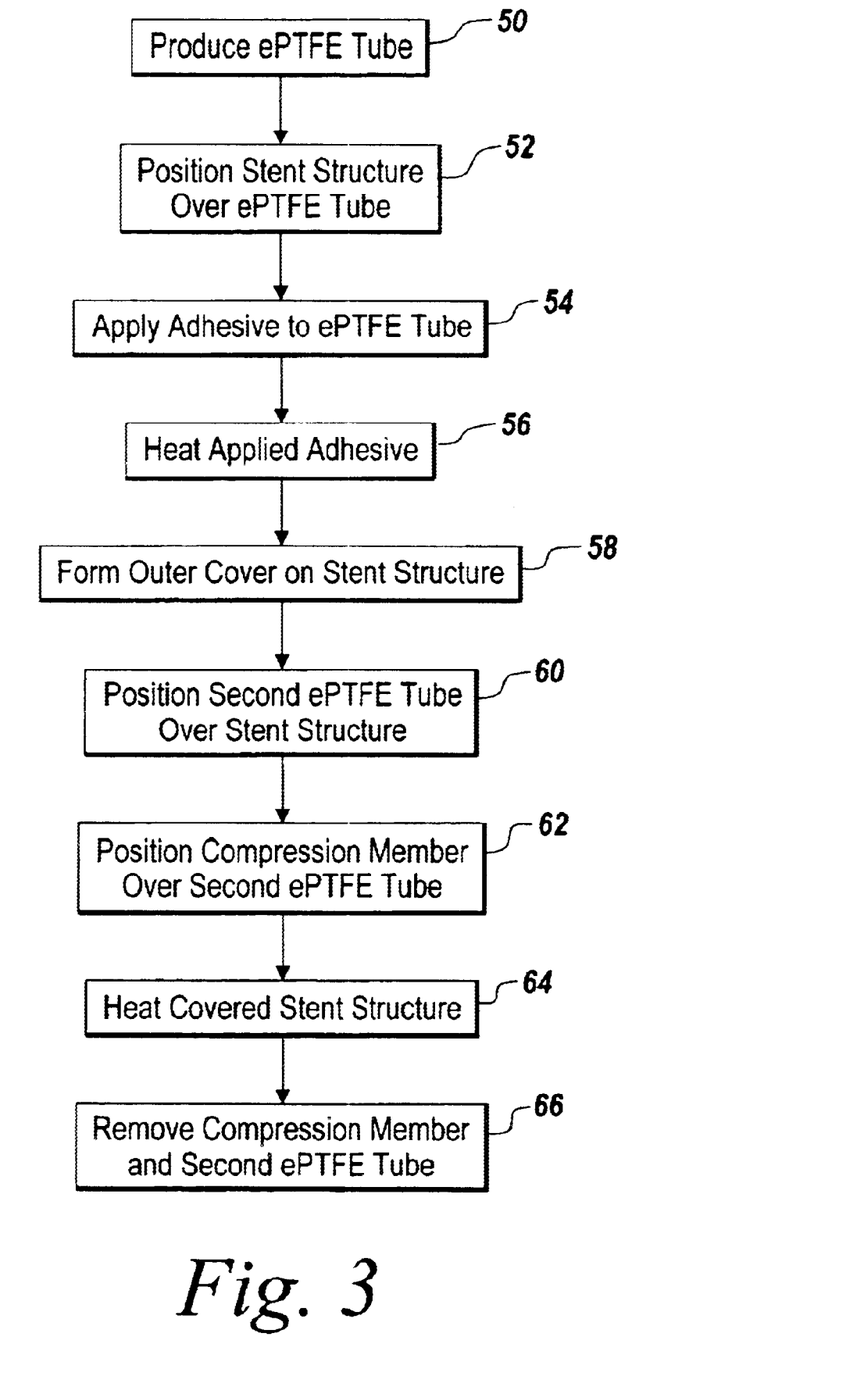
FIG. 3 is a flow chart illustrating a method of covering a stent according to the teachings of the present invention.

A method of covering a stent in accordance with the present invention is illustrated in the flow chart of FIG. 3. To form the inner cover of the stent covering, a tube of ePTFE is produced, step 50. The ePTFE tube is preferably produced through an extrusion and a longitudinal expansion process. An exemplary extrusion and expansion process is described below, however, one skilled in the art will appreciate that alternative processes for producing an ePTFE tube may be utilized without departing from the scope of the present invention. According to the exemplary process, a billet comprising a PTFE resin mixed with an organic lubricant is utilized. Various organic lubricants are suitable such as naphtha, ISOPAR-G and ISOPAR-H available from Exxon Corporation. The blended resin is compressed at low pressure to yield a tubular billet of PTFE resin and lubricant. The tubular billet is then extruded through an extruder, for example a ram extruder, to reduce the cross section of the billet and to yield a tubular extrudate. The organic lubricant can be removed from the extrudate by drying the extrudate in a heated oven. Once the tubular extrudate is produced, the extrudate is expanded by longitudinal stretching. After the extrudate has been stretched, it is heat set to lock in the microstructure of the material to complete the process of the forming the tube of ePTFE.

One skilled in the art will appreciate that the inner cover of the stent can be formed by other known methods of covering or coating without departing from the scope of the present invention. For example, the inner cover can be constructed from tape or wrap of ePTFE or other material that can be wrapped about a mandrel to form the inner cover.

The stent structure is placed over the ePTFE tube, step 52, preferably after mounting the ePTFE tube on a mandrel. The stent structure is preferably covered in the reduced diameter, unexpanded configuration. An adhesive can be optionally applied to the ePTFE tube to facilitate bonding of the ePTFE tube to the outer cover, step 54. The adhesive can be applied directly to the ePTFE tube, or can be applied to the outer covering. Any adhesive suitable for bonding ePTFE, or other covering materials, can be used. A preferred adhesive is an aqueous dispersion of PTFE, such as FLUON™ AD1, available from ICI Fluoropolymers of Wilmington, Del. If an aqueous dispersion of ePTFE is utilized as the adhesive, the aqueous dispersion is heated after application to evaporate the aqueous component of the dispersion, step 56.

The outer cover is then provided on the stent structure, step 58. The outer cover can be a separate tube of ePTFE or other suitable material, a wrap of fluoropolymer material such as a wrap of TEFLON tape, or other suitable covering materials. In one preferred embodiment, the ePTFE tube forming the inner cover is folded over the outer surface of the stent structure to form the outer cover. An exemplary method of covering a stent structure in this manner is described in commonly owned U.S. Pat. No. 6,010,529, incorporated herein by reference.

Figure 4:
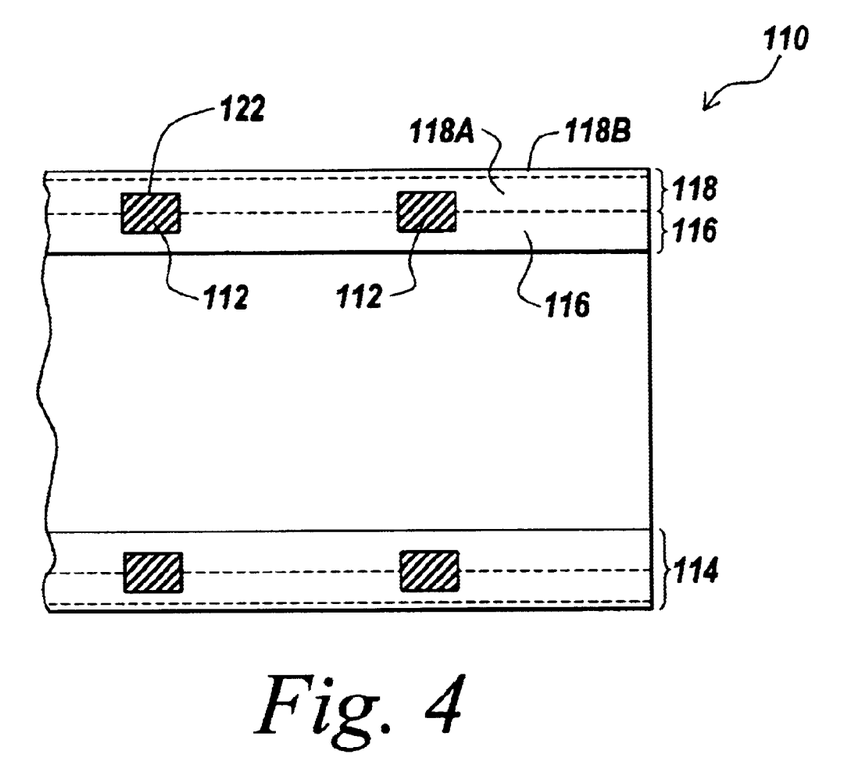
FIG. 4 is a side elevational view in cross-section of an end of a cover stent according to the teachings of the present invention.

FIG. 4 illustrates one end of an exemplary covered stent 110 in which the inner cover 116 is folded over the outer surface 122 of the stent structure 112 to form the outer cover 118. This embodiment provides a two-layer outer cover 118. The stent structure 112 can be covered by initially selecting an ePTFE tube for forming the inner cover 116 that is longer than the stent structure 112. The stent structure 112 is positioned coaxially external to and centrally along the length of the ePTFE tube. A first portion of the ePTFE tube extending from one end of the tube can be folded over the stent structure into contact with the outer surface 122 of the stent structure 112, to form the first outer cover layer 118A. A second portion of the ePTFE tube extending from the other end of the stent structure 112 then can be folded over the stent structure 112 into contact with the first portion of the ePTFE tube, to form the second cover layer 118B. This results in the outer cover 118 having two layers, 118A and 118B, corresponding to the portions of the ePTFE tube extending from the stent structure.

Referring again to FIG. 3, once the outer cover is in place, a second tube of ePTFE or other material is placed over the covered stent, step 60. A compression tube is positioned over the second tube of ePTFE, step 62. The compression tube and the second ePTFE tube are selected to have an inner diameter that is less than the diameter of the outer cover of the covered stent. The length of the compression tube and length of the second ePTFE tube each are preferably greater than or equal to the length of stent structure. It is important for the second tube to be constructed from a material that will not bond to ePTFE and for the compression tube to be constructed from a material that will not bond to the second tube. Preferable materials for the compression member tube include, but are not limited to, metal and metal alloys, such as stainless steel.

The covered stent structure is heated with the compression tube and the second ePTFE tube in place, step 64. The compression tube and second tube compress the covering material during heating, thereby forcing together the inner cover and the outer cover around the stent structure. Thus, the compression tube and second tube operate to facilitate the bonding of the inner cover to the outer cover. In addition, the compression tube, second tube and mandrel maintain the outer and inner diameter of the covered stent constant during the heating process, allowing the covered stent to be manufactured to a predetermined and predictable initial diameter. After heating, the compression tube, second ePTFE tube and mandrel are removed, step 66.

One skilled in the art will appreciate that the use of the compression tube and/or the second tube of ePTFE is optional. Heating of the covered stent can be sufficient to effect bonding of the inner cover to the outer cover. In addition, the inner cover and the outer cover are not limited to single layers. Additional layers of the same or different covering materials may be provided on the either the inner cover and/or the outer cover.

The properties of the stent covering can be adjusted by varying the process parameters used to create the ePTFE tube(s) used to form the stent covering. For example, the average IND of the stent covering can be adjusting by varying the amount of lubricant or the amount of PTFE resin used to create the PTFE billet. In addition, the average IND can be adjusted by varying the stretch rate and the stretch ratio of the expansion process. Likewise, the thickness of the stent cover can be adjusted by varying the thickness of the ePTFE tube(s) employed.

In one preferred embodiment, the stent covering is homogeneous, i.e. the fluoropolymer material selected for the inner cover is the same fluoropolymer material selected for the outer cover and the inner cover and the outer cover each have an identical or substantially similar average IND. The use of a homogeneous stent covering provides uniform and consistent expansion characteristics to the stent covering and can contribute to minimizing tearing of the stent covering during expansion. Thus, in one preferred embodiment, both the inner cover and the outer cover are constructed from ePTFE and the inner cover and the outer cover have an identical or substantially similar average IND that is greater than 100 microns.

One skilled in the art will appreciate that different materials can be used to form the inner cover and the outer cover, to provide a non-homogeneous or heterogeneous stent covering, without departing from the scope of the present invention. For example, a heterogeneous stent covering can be manufactured by forming the inner cover from a tube formed of a first material and forming the outer cover from a tube formed of a second material distinct from the first material.

Likewise, the average IND of the inner cover can be distinct from the average IND of the outer cover, to provide a stent covering having a non-uniform average IND, without departing from the scope of the present invention. For example, in certain applications it may be desirable to provide the outer cover with an average IND greater than the average IND of the inner cover, or vice versa, to modify the expansion characteristics of the covered stent. For example, a stent covering having a non-uniform average IND can be manufactured by forming the inner cover from a tube having a first average IND and by forming the outer cover from a tube having a second average IND, distinct from the first average IND. Alternatively, a single tube having an average IND that varies along its length can be used to form both the inner cover and the outer cover, in accordance with the folding method described above.

Regardless of whether the stent covering of the covered stent of the present invention is homogeneous or heterogeneous, or has a uniform or non-uniform average IND, it is preferable for either the inner cover or the outer cover of the stent covering to have an average IND greater than 100 microns.

EXAMPLE 1

Balloon expandable PALMAZ-type slotted stents were covered with ePTFE in accordance with the method of covering a stent described above. The expanded diameter of each stent was 9 mm. Each stent included an inner cover of ePTFE and a two-layer outer cover of ePTFE as illustrated in FIG. 4 above. The inner cover of each stent was formed from an ePTFE tube that was folded over the stent structure to create the outer cover of the covered stent.

A first lot of five stents, Lot 1 in Table 1 below, were covered using an ePTFE tube having an average wall thickness 0.0073 in. and an average IND of 137 microns. A second lot of five stents, Lot 2 in Table 1 below, were covered using an ePTFE tube having an average wall thickness of 0.010 in and an average IND of 139. A third lot of four stents, Lot 3 in Table 1 below, were covered using an ePTFE tube having an average wall thickness of 0.016 in and an average IND of 147. After covering, the cover wall thickness of each stent in the three lots was 0.009 in. Cover wall thickness refers to the thickness of the stent covering, measured between the elements of the stent structure, when the covered stent is in the unexpanded state.

Each of the stents was expanded once using a 9 mm PET balloon. The average deployment pressure of each lot of stents was determined. The results of the tests are set forth in Table 1.

TABLE 1

| Covered Stent | ePTFE Tube Wall Thickness (in.) | Cover Wall Thickness (in.) | Average IND (microns) | Avg. Deployment Pressure (ATM) |
|---|---|---|---|---|
| 1 | 0.0073 | 0.009 | 137 | 4.6 |
| 2 | 0.01 | 0.009 | 139 | 5.4 |
| 3 | 0.016 | 0.009 | 147 | 7.4 |

Each covered stent deployed to the 9 mm expanded configuration at relatively low average deployment pressures, i.e. less than 10 atm, and, more particularly, in the 4 atm to 8 atm range. Holes were observed in the covering of the stents of Lot 1 during expansion of the covered stent to the 9 mm expanded configuration. No holes or tearing were observed in the stent covering of the stents of Lots 2 and 3. The covered stents of Lots 2 and 3 each successfully deployed to the 9 mm expanded configuration with the stent covering intact.

EXAMPLE 2

Animal studies were conducted in which eight covered stents were deployed in the arteries of two male pigs to observe the cellular response to the stents. The stents employed were balloon expandable stents of the type described in commonly-assigned U.S. patent application Ser. No. 09/628,096, filed concurrently herewith. The stents were covered in accordance with the method described above. A single ePTFE tube was utilized to provide the inner cover and the outer cover. The stents had expanded diameters of 6–8 mm. The ePTFE used to cover each stent had a wall thickness of 0.01 in. and an average IND of 139 microns in the unexpanded configuration.

The covered stents were deployed in the left carotid artery, the right carotid artery, the left iliac artery, and the right iliac artery of two male pigs. The covered stents were deployed with a catheter delivered PET balloon using standard operative techniques. Each stent deployed successfully at approximately 6 atm. The pigs were sacrificed after 28 days. The stented vessels were explanted at the time of sacrifice and prepared for histology slides.

Figure 5A:
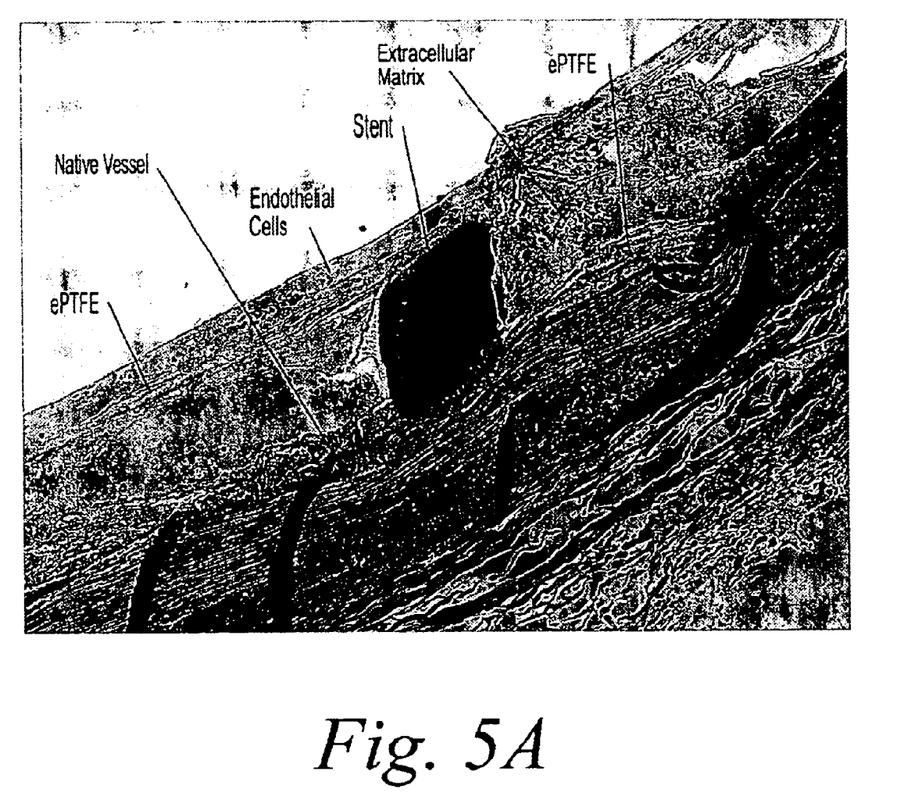
FIGS. 5A–C are histology slides of a covered stent of the present invention deployed in the right iliac artery of a male pig.
Figure 5B:
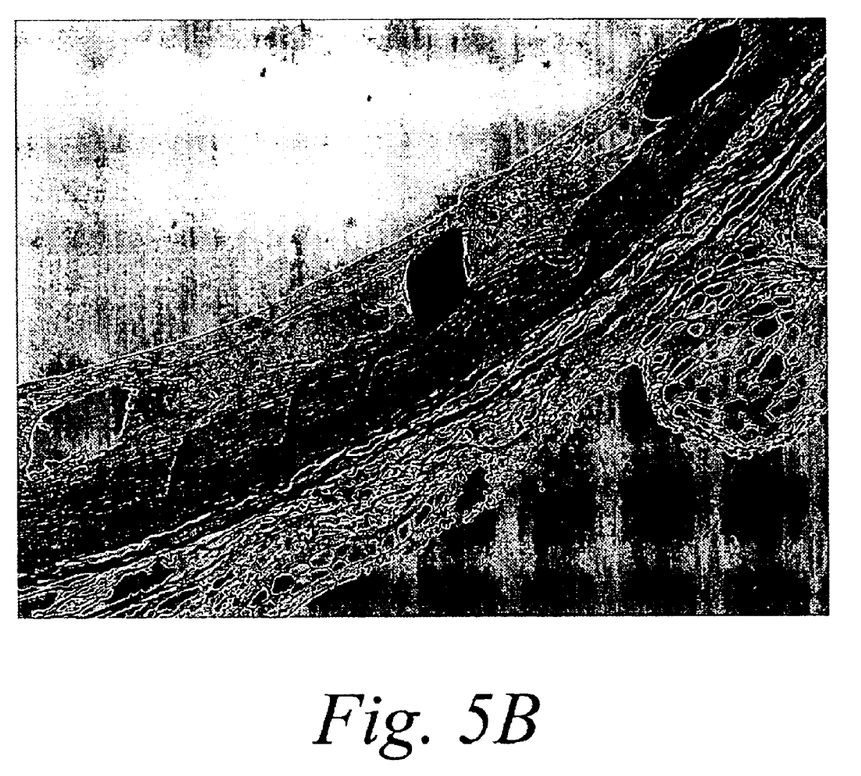
Figure 5C:
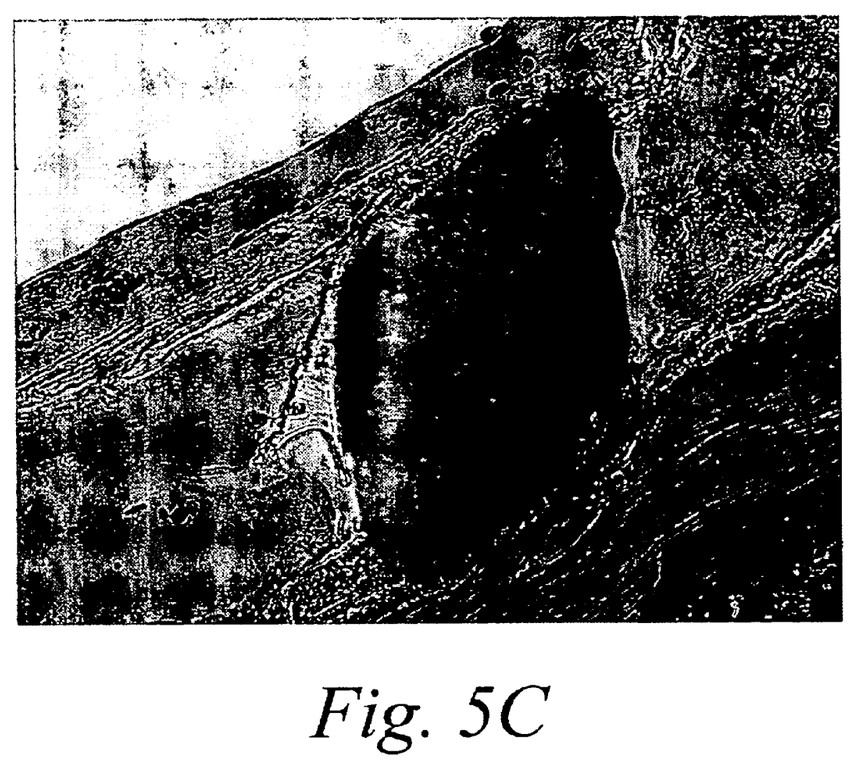

FIGS. 5A–C are histology slides at varying magnifications (20×, 10× and 50×, respectively) of the middle of one of the stents deployed in the right iliac artery of a 27 kg male pig. The histology slides illustrate the presence of only a thin layer of endothelial cells indicating no hyperplasia.

Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and desired to be secured by Letters Patent is:

1. A radially deployable stent comprising:
   a stent structure having an inner surface and an outer surface, and
   a stent covering comprising
   an inner cover of biocompatible material positioned adjacent said inner surface of said stent structure, and
   an outer cover of biocomparible material positioned adjacent said outer surface of said stent structure,
   wherein at least one of said biocompatible material of said inner cover and said biocompatible material of said outer cover has a predetermined thickness and has an average internodal distance (IND) of greater than 100 microns to reduce a deployment pressure necessary to expand the stent To less than 10 atmospheres.

2. The stent of claim 1, wherein said inner cover is folded over said outer surface of said stent structure to form said outer cover.

3. The sent of claim 1, wherein, a first portion of said inner cover is folded over said outer surface of said stent structure and a second portion of said inner cover is folded over said first portion of said inner cover.

4. The stent of claim 1, wherein said inner cover and said outer cover extend substantially along the entire length of said stent structure.

5. The stent of claim 1, wherein said average internodal distance (IND) of each of the inner cover and the outer cover of greater than 110 microns.

6. The stent of claim 1, wherein said average internodal distance (IND) of each of the inner cover and the outer covet of greater than 135 microns.

7. A radially deployable stent comprising:
   a stent structure having an inner surface and an outer surface, and
   a stent covering comprising
   an inner cover of biocompatible material positioned adjacent said in surface of said stent structure, and
   an outer cover of biocompatible material positioned adjacent said outer surface of said stent structure,
   wherein said stent covering has a radial thickness of at least about 0.008" and the average internodal distance (IND) of each of the inner cover and the outer cover of greater than 100 microns to reduce a deployment pressure necessary to expand the stent to less than 10 atmospheres.

8. The stent of claim 7, wherein said inner cover is folded over said outer surface of said stent structure to form said outer cover.

9. The stent of claim 8, wherein a first portion of said inner cover is folded over said outer surface of said stent structure and a second portion of said inner cover is folded over said first portion of said inner cover.

10. The stent of claim 7, wherein said inner cover and said outer cover extend substantially along the entire length of said steal structure.

11. The stent of clam 7, wherein sad avenge internodal distance (IND) of each of the inner cover and the outer cover of greater than 110 microns.

12. The stent of claim 7, where said average internodal distance (IND) of each of the inner cover and the outer cover of greater than 135 microns.

* * * * *